United States Patent [19]

Jayne et al.

[11] 4,147,640
[45] Apr. 3, 1979

[54] LUBRICANT COMPOSITION

[75] Inventors: Gerald J. J. Jayne, Wokingham, England; David R. Woods, Tavin Oranmore, Ireland; Joseph P. O'Brien, Kirkwood, Mo.

[73] Assignee: Edwin Cooper and Company Limited, Bracknell, England

[21] Appl. No.: 825,252

[22] Filed: Aug. 17, 1977

[30] Foreign Application Priority Data

Sep. 24, 1976 [GB] United Kingdom ............... 39822/76

[51] Int. Cl.² .................. C10M 1/38; C10M 3/32; C07G 17/00; C09B 49/00
[52] U.S. Cl. .................................. 252/45; 252/406; 260/139
[58] Field of Search ................. 252/31, 45, 406; 260/139

[56] References Cited

U.S. PATENT DOCUMENTS

| 2,312,750 | 3/1943 | Cohen | 252/45 |
| 2,337,473 | 12/1943 | Knowles et al. | 252/45 |
| 2,422,275 | 6/1947 | Winning et al. | 252/45 |
| 2,445,983 | 7/1948 | Watson | 252/45 |
| 2,500,167 | 3/1950 | Garwood et al. | 252/45 |
| 2,658,900 | 11/1953 | Stevens et al. | 252/45 |
| 2,817,653 | 12/1957 | Cole et al. | 252/45 |
| 4,000,078 | 12/1976 | Baldwin et al. | 252/45 |

FOREIGN PATENT DOCUMENTS 658128 5/1939 Fed. Rep. of Germany ............ 252/45

Primary Examiner—Irving Vaughn
Attorney, Agent, or Firm—Donald L. Johnson; Robert A. Linn; Joseph D. Odenweller

[57] ABSTRACT

Lubricating oils having improved antioxidant and antiwear properties are obtained by adding a minor amount of a reaction product made by reacting an olefinic hydrocarbon containing about 6–18 carbon atoms and about 1–3 olefinic double bonds concurrently with sulfur and hydrogen sulfide to obtain a reaction intermediate and reacting this intermediate with additional olefin hydrocarbon which may be the same or different. Preferred olefinic hydrocarbons are dicyclopentadiene and alloocimene.

24 Claims, No Drawings

LUBRICANT COMPOSITION

BACKGROUND

This invention relates to sulfurized products having utility as lubricant additives and lubricating compositions containing them. The invention also relates to a process for preparing sulfurized products, the products so prepared and lubricating compositions containing such products.

Antioxidant additives used in lubricating oils, particularly, but not exclusively, automotive lubricants, require a combination of properties which is difficult to meet in practice. Such additives must, of course, impart a high degree of resistance to oxidation to the lubricant, but in addition must be reasonably inexpensive, must be compatible with various other additives commonly used in lubricants, must have adequate thermal stability and must satisfy various other criteria of suitability, such as the ability to protect copper-lead bearings from corrosion. Very many different types of antioxidants have been proposed, and in some cases have been commercially used on a comparatively small scale. However, for many years the type of antioxidants which have been very widely used as the most suitable general purpose antioxidants for automotive and other lubricants are metal, particularly zinc, salts of di-hydrocarbyl dithiophosphoric acids.

However, the need for lubricant developments to keep pace with engine developments has given rise recently to difficulties in the use of metal dithiophosphate salts as antioxidants. The metal content of these additives is a source of ash and there is a growing tendency for the quality standards laid down by manufacturers and other interested organizations to specify low-ash lubricant formulations for modern engines. Attempts have been made to develop dithiophosphate derivatives, which do not contain metal, in order to meet these requirements. However, such developments have been forstalled, at least to some extent, by yet another development in engine design, namely, the use of catalytic devices in engine exhausts to minimize pollution caused by vehicle emissions. The catalysts used in such devices are sensitive to phosphorus compounds and can become poisoned and ineffective if exposed to such compounds. Consequently, the need has arisen for antioxidants which do not contain metal or phosphorus, and yet still meet all the requirements for antioxidants formerly satisfied by the metal dithiophosphates.

Sulfurized norbornenyl compounds are known and are reported by Kurtz et al., U.S. Pat. No. 3,586,700. Vulcanizing agents made by reaction of sulfur with diolefins such as dicyclopentadiene are reported by Mirviss, U.S. Pat. No. 3,523,926. German Pat. No. 658,128 discloses the reaction of unsaturated aliphatic compounds such as rubber with sulfur and hydrogen sulfide.

DESCRIPTION OF THE PREFERRED EMBODIMENTS

A preferred embodiment of this invention is a lubricating oil additive prepared by the process comprising:

(A) reacting about one mole of a first reactive olefin hydrocarbon containing about 6–18 carbon atoms and 1–3 olefin double bonds concurrently with about 0.1–5 moles of elemental sulfur and about 0.1–1 mole of hydrogen sulfide to obtain an intermediate, and (B) reacting at about 100°–210° C. said intermediate with about 0.2–1 moles of a second reactive olefinic hydrocarbon containing about 6–18 carbon atoms and 1–3 olefinic double bonds to obtain an oil soluble lubricating oil additive.

The olefinic hydrocarbons used in the initial stage may be any olefin hydrocarbon which contains an olefinic double bond which is reactive with sulfur and hydrogen sulfide. This is readily determined by merely mixing sulfur with the olefin and injecting hydrogen sulfide under reaction conditions. The initial reaction forms polysulfide bonds between the olefins.

Preferred olefins contain at least 5 carbon atoms. Although there is no real upper limit, it has been found that the more preferred olefins contain from 6 to about 18 carbon atoms. The olefins can be monounsaturated or polyunsaturated as long as one of the double bonds is activated to react with sulfur and hydrogen sulfide. In general, the reactive olefin contains from one to about three olefinic double bonds.

Examples of the above class of reactive olefinically unsaturated hydrocarbons include isoprene, cyclopentene, methylcyclopentene, cyclohexene, ocetent-1, limonene, norbornene, norbornadiene, octadecene, styrene, α-methyl-styrene, and the like.

The more preferred olefinically unsaturated hydrocarbons are alloocimene, i.e., 2,6-dimethyl-2,4,6-octatriene, and cyclopentadiene dimers including dicyclopentadiene and lower $C_{1-4}$ alkyl substituted cyclopentadiene dimers such as methylcyclopentadiene dimer.

The ratio of reactants used in the initial stage can vary widely. If excess sulfur is used, it can merely be filtered off after the reaction. An excess of hydrogen sulfide is not necessary, but is usually used. It can be injected into the reaction mixture containing olefin and sulfur and the excess passed out in the off-gas and trapped by suitable scrubbing means. Alternatively, the hydrogen sulfide reaction may be carried out in a closed vessel under pressure to increase the reaction rate. In general, good results can be obtained using about 0.1–5 moles of elemental sulfur and 0.1–1 mole of hydrogen sulfide per mole of reactive olefin. A more preferred range is about 1.5–2.5 moles of sulfur and 0.4–0.6 mole of hydrogen sulfide per mole of reactive olefin. Excellent results were obtained using about 2 moles of sulfur and 0.5 mole of hydrogen sulfide per mole of reactive olefin.

The initial stage should be conducted at a temperature high enough to cause reaction but not so high as to cause degradation of the reactants or products. A useful temperature range is about 0°–200° C. A preferred temperature range is about 50°–160° C. and a most preferred range is about 90°–120° C.

The initial reaction is preferably carried out using a sulfurization catalyst. These are well-known and include quaternary ammonium salts, guanidines, thiuram sulfides and disulfides, sodium dialkyldithiocarbamates, alkyl and cycloalkyl amines, such as n-butylamine, di-n-butylamine, n-octylamine, triethylamine, diisopropylamine, dicyclohexamine, and cyclohexylamine. Other catalysts are diethanolamine
triethanolamine
diphenyl guanidine
tetramethyl thiuram sulfide
tetramethyl thiuram disulfide
dipentamethylene thiuram tetrasulfide cyclohexylethylamine
piperidine
benzyl trimethylammonium hydroxide
sodium dibutyl dithiocarbamate, and the like.

The preferred catalysts are the alkyl amines such as methylamine, dimethylamine, ethylamine, diethylamine, 2-ethylhexylamine, dodecylamine, hexadecylamine, eicosylamine and the like.

The most preferred amines are the tert-alkyl primary amines. Such amines are available commercially such as Primene JM-T and Primene 81-R (registered trademark Rohm and Haas). These are mixtures of tert-alkyl primary amines the former containing about 18-22 carbon atoms per molecule and the latter containing about 12-14 carbon atoms per molecule.

The amount of sulfurization catalyst conventionally used is small, generally about 0.1-5 percent based on the olefin.

Reaction time is not an independent variable and depends on reaction conditions. The initial reaction should be conducted until the sulfurization is substantially complete as evidenced by the disappearance of sulfur and a sharp drop in the rate of hydrogen sulfide up-take. Good results are generally obtained in about 0.5-8 hours.

Following the initial stage of the reaction, the second stage is carried out. In the second stage, additional reactive olefin is added and the mixture heated to cause further reaction. The reactive olefins used in the second stage are of the same type used in the initial stage, but need not be the same specific olefin. For example, dicyclopentadiene can be used in the first and second stage or if desired alloocimene can be substituted in the second stage with good results. Likewise, alloocimene can be used in the first and second stage or dicyclopentadiene can be substituted in the second stage. Other reactive olefins which can be used in the second stage are styrene, limonene and norbornylene.

The additive can be prepared in a single stage by combining all olefin and sulfur and adding hydrogen sulfide in amounts to provide the same overall ratio as in the two-stage embodiment. In the single stage process the reaction is first heated at about 90°-120° C. until the sulfur reacts and then heated to about 130°-210° C., more preferably 130°-180° C., to complete the reaction.

Preferably the reaction is carried out in two stages. The effect of the second stage reaction is to reduce the corrosivity of the product. The product obtained by the two-stage process is generally superior to that obtained in a one-stage process employing the same overall amount of reactive olefin although carrying out the process in one stage is within the invention. Use of increased amounts of reactive olefin in the second stage leads to increased oil solubility, but lowers the sulfur content of the product. The amount of reactive olefin used in the second stage can vary widely. A useful range is about 0.2-1.0 moles of reactive olefin per mole of reactive olefin used in the initial stage of the reaction. A more preferred range is about 0.4-0.8 mole per mole of reactive olefin used in the initial stage. Very good results have been obtained using 0.6 mole of reactive olefin in the second stage per mole of reactive olefin used in the initial stage.

The second stage should be carried out at a temperature high enough to cause reaction but not so high as to cause insoluble materials to form. The optimum temperature varies somewhat with the materials used. In general, a reaction temperature above about 100° C. is desirable. Temperatures much above 210° C. have caused formation of some insoluble materials, although most of the product remained oil soluble. Accordingly, a useful range is about 100°-210° C. A more preferred temperature range is about 130°-180° C. and a highly recommended range is 150°-170° C.

The second reaction stage should be conducted for a time adequate to maximize the formation of an oil-soluble non-corrosive product. At higher temperatures a shorter reaction time is used than at lower temperatures. Reaction times of from about 15 minutes to 4 hours are useful. A preferred range is about 30 minutes to 3 hours.

A catalyst is preferably used in the second stage. For instance, it has been found that 2,5-dimercapto-1,3,4-thiadiazole, 2,5-bis(t-octyldithio)-1,3,4-thiadiazole and 2-(t-dodecyldithio)-5-mercapto-1,3,4-thiadiazole may be employed in the second stage with particular advantage.

Accordingly, a preferred catalyst for use in the second stage is a thiadiazole having the formula

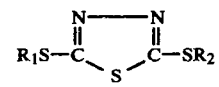

wherein $R_1$ and $R_2$ are independently selected from hydrogen or $-SR_3$, wherein $R_3$ is alkyl (e.g. methyl, tert-octyl, tert-dodecyl and the like).

Solvents are not required in either the initial or second-stage reaction. However, inert solvents such as neutral mineral oil, process oil, dimethylformamide, toluene, petroleum ether (80°-100° C.) and the like can be used if desired.

The following examples illustrate the manner of preparing additives of the invention.

EXAMPLE 1

In a reaction vessel was placed 264 g (2 m) of dicyclopentadiene, 128 g (4 m) of sulfur and 3.9 g of di-n-butylamine. The mixture was stirred at 80°-90° C. while hydrogen sulfide was injected into the liquid phase. An exothermic reaction occurred. After 4 hours hydrogen sulfide up-take had about stopped.

In a second stage 132 g (1 m) of dicyclopentadiene was added and while stirring the solution was heated to 160° C. Stirring was continued one hour at 160°-170° C. The product was heated in hot petroleum ether (bp 62°-68° C.) and filtered. It was vacuum stripped of volatiles to yield 487 g of a viscous product analyzing 29.2 percent sulfur.

EXAMPLE 2

In a reaction vessel was placed 264 g (2 m) of dicyclopentadiene, 128 g (4 m) of sulfur and 3.9 g of di-n-butylamine. The mixture was stirred at 80°-90° C. while hydrogen sulfide was injected. The reaction exotherm was sufficient to maintain 80°-90° C. temperature requiring some cooling. Hydrogen sulfide injection was continued until temperature dropped. A total of 92.7 g of hydrogen sulfide was passed into the liquid phase of which 30.9 g reacted, the remainder being trapped in the off-gas.

The mixture was blown with nitrogen to remove hydrogen sulfides and 132 g (1 m) of dicyclopentadiene added. The solution was heated to 160° C. and stirred at that temperature for 30 minutes. It was then cooled, diluted with petroleum ether and filtered. Nothing appeared to be removed on the filter. The product was stripped of volatiles under vacuum yielding 507 g of a dark viscous oil soluble liquid analyzing 29.7 percent sulfur.

EXAMPLE 3

This example was conducted the same as Example 2 except the initial reaction was carried out at 90°–100° C. using 32.3 g of hydrogen sulfide over a one-hour period. In the second stage 145 g (1.1 m) of dicyclopentadiene was added and the mixture reacted 30 minutes at 180° C. The product analyzed 27.9 percent sulfur.

EXAMPLE 4

In this reaction all the reactants were reacted in a single stage. In a reaction vessel was placed 264 g (2 m) of dicyclopentadiene, 64 g (2 m) sulfur and 3.9 g di-n-butylamine. The mixture was stirred at 90°–100° C. while injecting hydrogen sulfide. A total of 31.4 g of hydrogen sulfide reacted. The product was blown with nitrogen, filtered and vacuum stripped giving a light colored viscous product having good oil solubility analyzing 26.4 percent sulfur. It gave a 4c rating in a Copper Strip Corrosion Test at 1 percent in an oil solution after 1.5 hours (ASTM-D-130-68).

EXAMPLE 5

In a reaction vessel was placed 264 g (2 m) of dicyclopentadiene, 128 g (4 m) sulfur and 3.9 g di-n-butylamine. Hydrogen sulfide was injected at 90°–110° C. giving an exothermic reaction and taking up 32.7 g of hydrogen sulfide.

In the second stage 112 g (1 m) of octene was added and reacted 3 hours at 160° C. The product was vacuum stripped and filtered, giving a dark viscous product.

EXAMPLE 6

In a reaction vessel was placed 264 g (2 m) of dicyclopentadiene, 128 g (4 m) sulfur and 3.9 g di-n-butylamine. The mixture was stirred at 100°–120° C. for 2 hours while injecting hydrogen sulfide. A total of 31 g of hydrogen sulfide reacted.

In the second stage 158.4 g (1.2 m) of dicyclopentadiene was added and the solution stirred at 165°–175° C. for 30 minutes. The reaction yielded 560 g of a viscous liquid product useful as a lubricant antioxidant antiwear agent.

EXAMPLE 7

An intermediate product was prepared by reacting 528 g (4 m) of dicyclopentadiene, 256 g (8 m) of sulfur, 7.8 g of di-n-butylamine and 62 g of hydrogen sulfide at 90°–100° C.

A 106.5 g portion of the above intermediate was placed in a separate reaction vessel to which was added 34 g (0.25 m) of alloocimene and the mixture heated one hour at 170°–180° C. This gave 140 g of a viscous liquid product which was oil soluble except for a few particles. It analyzed 27.3 percent sulfur and gave a 2a-3b copper strip rating.

EXAMPLE 8

A stock batch of intermediate was prepared by reacting 528 g (4 m) of dicyclopentadiene, 256 g (8 m) of sulfur, 7.8 g of di-n-butylamine and 64 g of hydrogen sulfide at 90°–110° C. for 2 hours.

In a separate reaction vessel was placed 106.5 g of the above intermediate and 34 g alloocimene. The mixture was heated at 150° C. for 2 hours giving a viscous liquid oil-soluble product analyzing 29 percent sulfur. It gave a 2b-3b rating in the Copper Strip Corrosion Test.

EXAMPLE 9

In a reaction vessel was placed 264 g (2 m) of dicyclopentadiene, 128 g (4 m) of sulfur, 3.9 g of di-n-butylamine and 3.9 g of 2,5-bis(octyldithio)-1,3,4-dithiadiazaole. The mixture was reacted at 95°–100° C. during which 29 g of hydrogen sulfide was taken up.

In a second stage 145 g (1.1 m) of dicyclopentadiene was added and the solution reacted at 170° C. for 15 minutes. It was then filtered giving 550.1 g of a viscous oil-soluble liquid analyzing 27.6 percent sulfur.

EXAMPLE 10

In a reaction vessel was placed 264 g (2 m) of dicyclopentadiene, 128 g (4 m) of sulfur, 3.9 g of di-n-butylamine and 3.9 g of 2,5-bis(octyldithio)-1,3,4-thiadiazole. This mixture was stirred at about 95° C. while hydrogen sulfide was injected. A total of 26 g reacted.

Following this, 136 g (1 m) of alloocimene was added and the mixture stirred 2 hours at 150° C. It was filtered hot to give 540.6 g of liquid product analyzing 26.1 percent sulfur. It gave a 1b rating in the Copper Strip Corrosion Test.

EXAMPLE 11

In a reaction vessel was placed 132 g (1 m) of dicyclopentadiene, 48 g (1.5 m) of sulfur and 2 g of di-n-butylamine. The mixture was stirred at 90°–100° C. for one hour while hydrogen sulfide was injected. The uptake was 16.29 g.

A 98.5 g portion of the above intermediate was placed in a second vessel to which was added 15.75 g of di-cyclopentadiene. The mixture was heated at 150° C. for 2 hours yielding 108.5 g of liquid product analyzing 27.7 percent sulfur. Copper strip corrosion rating was 3b.

EXAMPLE 12

In a reaction vessel was placed 56.7 g of the intermediate from Example 11. To this was added 9 g of alloocimene and the mixture heated 2 hours at 150° C. yielding an oil-soluble product analyzing 22.4 percent sulfur, giving a 3b copper strip corrosion rating.

EXAMPLE 13

An intermediate was prepared by reacting a mixture of 528 g (4 m) of di-cyclopentadiene, 256 g (8 m) of sulfur and 7.8 g of di-n-butylamine with 63.2 g of hydrogen sulfide at 90°–110° C. over a 2-hour period.

In a separate reaction vessel was placed 426 g of the above intermediate, and 158.4 g (1.2 m) of di-cyclopentadiene. The mixture was stirred for 2 hours at 150° C. to give a liquid product analyzing 26.2 percent sulfur. Copper strip corrosion rating was 2a.

EXAMPLE 14

In a reaction vessel was placed 106.5 g of the intermediate prepared in Example 13. To this was added 34 g of alloocimene, and the mixture stirred 2 hours at 150° C. giving an oil-soluble product analyzing 28 percent sulfur. The copper strip corrosion rating was 2b-3a.

EXAMPLE 15

In a reaction vessel was placed 162 g (1 m) of methylcyclopentadiene dimer, 64 g (2 m) of sulfur and 2 g of di-n-butylamine. While stirring, hydrogen sulfide was injected giving a 16 g up-take. The intermediate was filtered and analyzed for sulfur (32.5 percent S).

In a second reaction vessel was placed 162 g of the above intermediate and 54 g of methylcyclopentadienyl dimer. The mixture was heated for 2 hours at 150° C. giving a dark viscous liquid product analyzing 23.3 percent sulfur.

EXAMPLE 16

In a reaction vessel was placed 38 g of the intermediate made in Example 13. To this was added 14.45 g of the methylcyclopentadienyl dimer and the mixture heated two hours at 150° C. giving a very dark liquid product analyzing 25.9 percent sulfur.

EXAMPLE 17

In a reaction vessel was placed 68 g (0.5 m) of dicyclopentadiene, 64 g (2 m) of sulfur and 2 g of di-n-butylamine. Hydrogen sulfide was injected at 90°–100° C. giving an 8.6 g up-take.

To this intermediate was added 102 g (0.75 m) of dicyclopentadiene and the mixture heated 2 hours at 150° C. The product was filtered giving a viscous liquid analyzing 29 percent sulfur and giving a 3b copper strip corrosion rating.

EXAMPLE 18

In a reaction vessel was placed 106.5 g of the intermediate from Example 13. To this was added 26 g of styrene and the mixture was heated for 2 hours at 150° C. giving a liquid product which exhibited a copper strip corrosion rating of 3b.

EXAMPLE 19

In a reaction vessel was placed 106.5 g of an intermediate from Example 13 and 39.6 g of di-cyclopentadiene. The mixture was heated at 150° C. for 2 hours giving a dark viscous liquid product analyzing 27 percent sulfur giving a 2c-3a copper strip corrosion rating.

EXAMPLE 20

In a reaction vessel was placed 42.6 g of the intermediate from Example 13, 15.9 g of dicyclopentadiene and 0.5 g of 2,5-dimercapto-1,3,4-thiadiazole. The mixture was heated at 150° C. for 2 hours giving a fairly mobile liquid product, lighter in color than that of all previous Examples and giving a 1b-2a copper strip corrosion rating.

EXAMPLE 21

In a reaction vessel was placed 528 g (4 m) of dicyclopentadiene, 256 g of sulfur (8 m) and 12 g of Primene 81-R. The mixture was stirred at 90° C. and $H_2S$ injected while keeping the temperature at about 110° C. Uptake of $H_2S$ stopped in about 75 minutes when 68 g had reacted.

In a second stage 317 g of dicyclopentadiene and 12 g of 2,5-dimercaptothiadiazole were added and the mixture stirred 30 minutes at 150° C. The product was vacuum stripped to remove volatiles (4 g) and filtered hot to yield 1139 g of product analyzing 25.7 wt percent sulphur.

EXAMPLE 22

In a reaction vessel was placed 66 g of dicyclopentadiene, 32 g of sulfur and 1.5 g of Primene 81-R. While stirring at 90° C., $H_2S$ was injected (8.2 g) over a 20 minute period.

In a second stage 39.6 g of dicyclopentadiene and 0.75 g of dimercaptothiadiazole was added and the mixture stirred at 150° C. for 30 minutes. It was then vacuum stripped and filtered yielding 140 g of product which gave a 3b copper strip test.

EXAMPLE 23

This run was conducted in a solvent. In a reaction vessel was placed 132 g of dicyclopentadiene, 64 g of sulfur, 50 ml toluene and 3 g Primene 81-R. The mixture was stirred at 90° C. and $H_2S$ injected (16 g) over a 30 minute period.

In a second stage 79.2 g of dicyclopentadiene and 3 g of dimercaptothiadiazole were added and the mixture stirred at 150° C. for 30 minutes. Solvent was stripped under vacuum and the product filtered to yield 268 g of product, analyzing 27.4 wt percent sulfur.

EXAMPLE 24

This run was conducted as in Example 23, except a polar solvent dimethyl formamide was used instead of toluene. The product was recovered in the same manner, yielding 265 g of product, analyzing 28.1 wt percent sulfur.

The additives are useful in lubricating oil compositions. This includes both mineral lubricating oil and synthetic lubricating oil such as olefin oligomers (i.e., decene-1 trimer), alkylated benzenes (e.g., octadecylbenzene) esters (e.g., di-2-ethylhexyladipate) and the like.

In lubricating oil compositions the additives are generally used in conjunction with other conventional oil additives such as neutral and overbased calcium or magnesium alkaryl sulfonates, phosphorosulfurized terpenes, phosphorosulfurized polyisobutylene, metal salts of phosphorosulfurized polyisobutylene, polyisobutyl succinimide of ethylene polyamines, polyisobutylphenol Mannich amine dispersants, N-alkylphenyl naphthylamine antioxidants, phenolic antioxidants such as 4,4'-methylene bis(2,6-di-tert-butylphenol) or N,N-dimethyl-3,5-di-tert-butyl-4-hydroxybenzyl amine and the like. Commercial lubricating oil conventionally contains a zinc dialkyldithiophosphate. When using the additives of the present invention, the amount of the zinc additive can be greatly reduced giving a low ash or no ash lubricant formulation.

In addition to crankcase lubricating oils, the additives of the present invention may also be useful in gear oils, transmission fluids, greases and the like.

The amount of the present additives used in lubricant compositions can vary from about 0.05 weight percent to about 10 weight percent. A more preferred range is about 0.5–2.5 weight percent and most preferably 0.5–1.5 weight percent.

Tests have been carried out to demonstrate the utility of the present additives. One test was the 4-Ball in which an EN 31 steel ball is rotated in loaded contact with 3 fixed similar balls. The contact is lubricated with a mineral oil solution of the test additive (IP 239/73T). Test criteria are the initial seizure load at which collapse of the oil film between the balls occurs, weld load and scar diameter at different loads. The test oil contained sufficient additive to provide 0.85% S in the oil blend. Table 1 gives the test results.

Table 1

| Additive | Initial Seizure Load (Kg) | Weld Point (Kg) |
|---|---|---|
| Base oil | 65 | 135 |
| Example 8 | 90 | 340 |
| Example 9 | 80 | 350 |
| Example 10 | 85 | 390 |

A second test was the Timken OK Load Test (IP 240/74). Additive concentration was sufficient to provide 0.3 percent sulfur in the base oil which was a 150 solvent neutral mineral oil. In this test, a test block bears against a rotating cup. The OK load is the maximum load at which no scoring or seizure occurs. Table 2 gives the results of this test.

Table 2

| Test Additive | Timken OK Load (lbs.) |
|---|---|
| None | 12 |
| Example 8 | 40 |
| Example 9 | 35 |
| Example 10 | 50 |

Antioxidant effectiveness was determined using the Rotary Bomb Test (IP 229/73T) in which 2 percent of the test additive is dissolved in neutral mineral oil. The oil is then placed in a test bomb under oxygen pressure. The bomb is rotated in a 150° C. bath and the minutes until a sharp pressure drop is recorded as the induction period. Table 3 shows the results obtained.

Table 3

| Test Additive | Induction period (min.) |
|---|---|
| Base oil | 42 |
| Example 9 | 176 |
| Example 10 | 135 |
| Example 11 | 172 |
| Example 14 | 140 |
| Example 17 | 196 |
| Example 19 | 290 |

Several of the additives were subjected to an extended 36 hour Petter WI Engine Test. In this test the lubricating oil was blended to contain 1% by weight of the test additive in a formulated mineral lubricating oil which contained other conventional oil additives (e.g., succinimide dispersant, overbased magnesium sulfonate, zinc dialkyldithiophosphate, etc.) Bearing weight loss was measured and the appearance of the piston after the test was rated on a scale of 0-10 (10 = clean). Table 4 gives the the results of this test.

Table 4

| Test Additive | Bearing Wt. Loss (mg) | Piston Rating Skirt | Piston Rating Undercrown |
|---|---|---|---|
| Example 8 | 30 | 9.0 | 8.0 |
| Example 9 | 14 | 10.0 | 8.0 |
| Example 10 | 22 | 10.0 | 9.3 |
| Example 13 | 36 | — | — |
| Example 21 | 25 | 9.9 | 7.2 |

For comparison, an otherwise identical oil except containing a phosphosulfurized terpene in addition to a zinc dialkyl dithiophosphate, a metal sulfonate detergent, a polymethacrylate VI improver, a succinimide dispersant and a combination of corrosion inhibitors gives about a 15 mg bearing weight loss after 36 hours.

We claim:

1. A lubricating oil additive prepared by the process comprising:
    (A) in a first stage reacting at about 50°-160° C. about one mole of a first reactive olefinically unsaturated hydrocarbon containing about 6-18 carbon atoms and 1-3 olefinic double bonds with about 0.1-5 moles of elemental sulfur and about 0.1-1 moles of added hydrogen sulfide to obtain an intermediate, and
    (B) in a second stage reacting at about 100°-210° C. said intermediate with about 0.2-1 moles of a second reactive olefinically unsaturated hydrocarbon containing about 6-18 carbon atoms and 1-3 olefinic double bonds, said second olefinically unsaturated hydrocarbon being the same or different from said first olefinically unsaturated hydrocarbon, to obtain an oil soluble lubricating oil additive.

2. An additive of claim 1 wherein said first reactive olefinically unsaturated hydrocarbon and said second reactive olefinically unsaturated hydrocarbons are selected from the group consisting of cyclopentadiene dimers, lower alkylcyclopentadiene dimers and alloocimene.

3. An additive of claim 2 wherein said first and said second reactive olefinically unsaturated hydrocarbons are dicyclopentadiene.

4. An additive of claim 2 wherein said first and said second reactive olefinically unsaturated hydrocarbons are alloocimene.

5. An additive of claim 2 wherein said first reactive olefinically unsaturated hydrocarbon is dicyclopentadiene and said second reactive olefinically unsaturated hydrocarbon is alloocimene.

6. An additive of claim 2 wherein said first reactive olefinically unsaturated hydrocarbon is alloocimene and said second reactive olefinically unsaturated hydrocarbon is dicyclopentadiene.

7. An additive of claim 2 wherein in step (A) said one mole of first reactive olefinically unsaturated hydrocarbon is reacted concurrently with about 0.4-0.6 mole of hydrogen sulfide and about 1.5-2.5 moles of sulfur and in step (B) said intermediate is reacted with about 0.4-0.8 mole of said second reactive olefinically unsaturated hydrocarbon.

8. An additive of claim 7 wherein said first reactive olefinically unsaturated hydrocarbon and said second reactive olefinically unsaturated hydrocarbon are alloocimene.

9. An additive of claim 7 wherein said first reactive olefinically unsaturated hydrocarbon and said second reactive olefinically unsaturated hydrocarbon are dicyclopentadiene.

10. An additive of claim 7 wherein said first reactive olefinically unsaturated hydrocarbon is dicyclopentadiene and said second reactive olefinically unsaturated hydrocarbon is alloocimene.

11. An additive of claim 7 wherein said first reactive olefinically unsaturated hydrocarbon is alloocimene and said second reactive olefinically unsaturated hydrocarbon is dicyclopentadiene.

12. A process for making a lubricating oil additive, said process comprising:
    (A) in a first stage reacting at about 50°-160° C. about one mole of a first reactive olefinically unsaturated hydrocarbon containing about 6-18 carbon atoms and 1-3 olefinic double bonds concurrently with about 0.1-5 moles of elemental sulfur and about 0.1-1 moles of added hydrogen sulfide to obtain an intermediate, and (B) in a second stage reacting at about 100°–210° C. said intermediate with about 0.2-1 moles of a second reactive olefinically unsaturated hydrocarbon containing about 6-18 carbon atoms and 1-3 olefinic double bonds to obtain an oil soluble lubricating oil additive.

13. A process of claim 12 wherein said first reactive olefinically unsaturated hydrocarbon and said second reactive olefinically unsaturated hydrocarbons are selected from the group consisting of cyclopentadiene dimers, lower alkylcyclopentadiene dimers and alloocimene.

14. A process of claim 13 wherein said first and said second reactive olefinically unsaturated hydrocarbons are dicyclopentadiene.

15. A process of claim 13 wherein said first and said second reactive olefinically unsaturated hydrocarbons are alloocimene.

16. A process of claim 13 wherein said first reactive olefinically unsaturated hydrocarbon is dicyclopentadiene and said second reactive olefinically unsaturated hydrocarbon is alloocimene.

17. A process of claim 13 wherein said first reactive olefinically unsaturated hydrocarbon is alloocimene and said second reactive olefinically unsaturated hydrocarbon is dicyclopentadiene.

18. A lubricating oil composition comprising a major amount of a lubricating oil and a minor amount sufficient to impart antioxidant properties of an additive of claim 1.

19. A lubricating oil composition of claim 18 wherein said first reactive olefinically unsaturated hydrocarbon and said second reactive olefinically unsaturated hydrocarbon are selected from the group consisting of cyclopentadiene dimers, lower alkylcyclopentadiene dimers and alloocimene.

20. A lubricating oil composition of claim 19 wherein said first and said second reactive olefinically unsaturated hydrocarbons are dicyclopentadiene.

21. A lubricating oil composition of claim 19 wherein said first and said second reactive olefinically unsaturated hydrocarbons are alloocimene.

22. A lubricating oil composition of claim 19 wherein said first reactive olefinically unsaturated hydrocarbon is dicyclopentadiene and said second relative olefinically unsaturated hydrocarbon is alloocimene.

23. A lubricating oil composition of claim 19 wherein said first reactive olefinically unsaturated hydrocarbon is alloocimene and said second reactive olefinically unsaturated hydrocarbon is dicyclopentadiene.

24. A lubricating oil composition comprising a major amount of a lubricating oil and a minor amount sufficient to impart antioxidant properties of an additive of claim 7.

* * * * *